US012751646B2

(12) United States Patent
McDaid

(10) Patent No.: US 12,751,646 B2
(45) Date of Patent: Oct. 6, 2026

(54) WEARABLE DEVICE FOR DETERMINING MOTION AND/OR A PHYSIOLOGICAL STATE OF A WEARER

(71) Applicant: OPUM TECHNOLOGIES LIMITED, Grafton (NZ)

(72) Inventor: Andrew John McDaid, New Lynn (NZ)

(73) Assignee: OPUM TECHNOLOGIES LIMITED, Auckland (NZ)

(*) Notice: Subject to any disclaimer, the term of this patent is extended or adjusted under 35 U.S.C. 154(b) by 355 days.

(21) Appl. No.: 17/781,293

(22) PCT Filed: Nov. 30, 2020

(86) PCT No.: PCT/NZ2020/050159
§ 371 (c)(1),
(2) Date: May 31, 2022

(87) PCT Pub. No.: WO2021/107790
PCT Pub. Date: Jun. 3, 2021

(65) Prior Publication Data

US 2022/0409098 A1 Dec. 29, 2022

(30) Foreign Application Priority Data

Nov. 29, 2019 (NZ) ........................................ 759643

(51) Int. Cl.
*A61B 5/11* (2006.01)
*A61B 5/00* (2006.01)
*A61B 5/0205* (2006.01)

(52) U.S. Cl.
CPC .......... *A61B 5/1114* (2013.01); *A61B 5/0205* (2013.01); *A61B 5/1116* (2013.01);
(Continued)

(58) Field of Classification Search
CPC ................ A61B 2562/0219; A61B 2562/0223
See application file for complete search history.

(56) References Cited

U.S. PATENT DOCUMENTS

2013/0041289 A1* 2/2013 Sena .................... A61B 5/4585 600/595
2016/0262687 A1* 9/2016 Vaidyanathan ...... A61B 5/0205
(Continued)

FOREIGN PATENT DOCUMENTS

DE 102012100980 B4 † 1/2023
WO WO 2019/023109 A1 2/2018
WO WO 2019/112969 A1 6/2019

OTHER PUBLICATIONS

PCT International Search Report for PCT/NZ2020/050159, filed Nov. 30, 2020, mailed Feb. 23, 2021, 5 pages.
(Continued)

*Primary Examiner* — Benjamin J Klein
*Assistant Examiner* — Thien Jason Tran
(74) *Attorney, Agent, or Firm* — Husch Blackwell LLP

(57) ABSTRACT

The invention relates to a wearable device for determining a nature of motion and/or a physiological state of a wearer. The wearable device comprises a body portion configured to be worn by the wearer and at least one sensor mounted to the body portion configured to, while the wearable device is being worn, detect a motion parameter of the wearer and/or a physiological parameter of the wearer and generate input data indicative of the motion parameter and/or the physiological parameter. The wearable device further comprises a processor configured to receive the input data from the at least one sensor and process the input data by executing an algorithm to determine the nature of motion and/or the physiological state of the wearer while the wearable device is being worn. The invention further relates to a system for
(Continued)

determining a nature of motion and/or a physiological state of a wearer.

16 Claims, 6 Drawing Sheets

(52) U.S. Cl.
CPC .......... *A61B 5/6807* (2013.01); *A61B 5/6812* (2013.01); *A61B 5/7267* (2013.01); *A61B 5/0022* (2013.01); *A61B 2562/0219* (2013.01); *A61B 2562/0223* (2013.01)

(56) References Cited

U.S. PATENT DOCUMENTS

| | | | | |
|---|---|---|---|---|
| 2017/0000389 | A1* | 1/2017 | Davidson | A61B 5/6828 |
| 2019/0038225 | A1* | 2/2019 | Leavitt | G16H 10/60 |
| 2019/0053762 | A1 | 2/2019 | Saigh | |
| 2019/0112969 | A1 | 4/2019 | Suh et al. | |
| 2019/0298998 | A1* | 10/2019 | Coleman | A61N 1/36014 |

OTHER PUBLICATIONS

PCT Written Opinion of the ISA for PCT/NZ2020/050159, filed Nov. 30, 2020, mailed Feb. 23, 2021, 8 pages.

* cited by examiner
† cited by third party

WEARABLE DEVICE FOR DETERMINING MOTION AND/OR A PHYSIOLOGICAL STATE OF A WEARER

RELATED APPLICATIONS

This application is a National Phase entry of PCT Application No. PCT/NZ2020/050159 filed Nov. 30, 2020, which application claims the benefit of priority to NZ Application No. 759643 filed Nov. 29, 2019, the entire disclosures of which are incorporated herein by reference.

FIELD OF THE INVENTION

The present invention relates to a wearable device such as an orthosis, exoskeleton, rehabilitation robot, prosthetic, smart watch, smart phone or other suitable computing device for determining motion and/or a physiological state of a wearer for use in a variety of applications.

BACKGROUND TO THE INVENTION

Wearable devices are useful to collect data from a human or animal wearer for various applications including but not limited to health and entertainment. In particular, the data collection and use may be associated with rehabilitation, support, monitoring, diagnosis or prevention of afflictions and/or injuries of a human or animal wearer, neuromuscular, skeletal and/or otherwise.

Several problems exist with the collection, processing, application and benefit of the data collected.

The raw data or input data collected from sensors which are configured on board the wearable devices is generated at a high frequency (e.g. 100 samples per second per sensor) and a large amount of data is therefore generated. The large amount of data makes it more difficult to process in order to obtain useful insights and/or transfer the data from the wearable device for remote processing, e.g. transferring the collected data from the wearable device to a cloud computing system such as a cloud-based server for processing.

Processors using Artificial Intelligence (AI) and machine learning algorithms are useful tools to provide insights using large and complex data. However, AI and machine learning are typically used to process data "offline".

One problem is that there are typically limited processing capabilities on board a wearable device due to the physical size thereof.

A second problem is that configuring (re-configuring, optimising, improving, modifying, altering, updating, training, and/or re-training) algorithms can be computationally expensive and require long periods of time to operate as well as large amounts of data.

A further problem is that wearers are different and the same wearer's ability to perform tasks may change over time and necessitate re-configuration of the algorithms. In one example, the wearer may be recovering from an injury and he/she has an impaired gait pattern (limp), or he/she is wearing a brace, the ability of the wearer to walk or perform other activities may change as they recover from the injury. In another example, the wearer may be pre-symptomatic and then develops symptoms over time, e.g. develops osteoarthritis.

It is an object of aspects of the technology to provide a wearable device for determining motion and/or a physiological state of the wearer to overcome or ameliorate problems with existing devices. Alternatively, it is an object to provide an improved device for and/or processor-implemented method of determining motion and/or a physiological state of a wearer. Alternatively, it is an object to at least provide the public with a useful choice.

SUMMARY OF THE INVENTION

According to aspects of the invention there is provided a wearable device, a system and/or a method for determining motion and/or a physiological state of a wearer by analysing data indicative of the wearer's motion and/or physiological state received from one or more sensors.

According to one aspect of the invention there is provided a system for determining motion and/or a physiological state of a user, the system comprising:

at least one sensor configured to in use detect and transmit input data relating to the user's motion and/or physiology;

a processor configured to in use process the input data received from the sensor, wherein the processor is configured to process the input data and generate output data, wherein the output data provides a determination of motion and/or the physiological state of the user.

In examples:

The sensor may be configured on a wearable device. A wearable device may comprise any device which is worn, held, carried by, attached to or mounted on a human or animal in any suitable manner or form, including wearable activity trackers, smart watches, smart phones, smart shoes and other devices able to be carried.

The processor may be comprised as part of the wearable device.

The processor may be located remote to the sensor.

The processor may be configured to process the input data and generate the output data by execution of a predetermined algorithm.

The processor may be configured to re-configure the predetermined algorithm based on the input data provided by the sensor and/or input data from a sensor of another wearable device.

The system may further comprise a determination processor configured to determine whether the processor to in use process the input data received from the sensor is a processor comprised as part of the wearable device processor and/or a processor located remote to the sensor.

The system may further comprise a determination processor configured to determine whether the re-configuration of the predetermined algorithm is carried out by a processor comprised as part of the wearable device and/or a processor located remote to the sensor.

According to another aspect of the invention there is provided a wearable device for determining motion and/or a physiological state of a wearer, the wearable device comprising:

at least one sensor configured to in use detect and transmit input data relating to the wearer's motion and/or physiology;

a processor configured to in use process the input data received from the sensor, wherein the processor is configured to process the input data and generate output data, wherein the output data provides a determination of motion and/or the physiological state of the wearer.

According to yet another aspect of the invention there is provided a wearable device for determining motion and/or a physiological state of a wearer, the wearable device comprising:

a sensor configured to in use detect and transmit input data relating to the wearer's motion and/or physiology;

a processor configured to in use process the input data received from the sensor, wherein the processor is configured to execute an algorithm designed to process the input data and generate output data, wherein the output data provides a determination of the motion being performed and/or the physiological state of the wearer, and wherein the processor is configured to configure the algorithm based on input data provided by the sensor and/or a sensor of another wearable device.

According to yet another aspect of the invention there is provided a wearable device for determining motion and/or a physiological state of a wearer, the wearable device comprising:

a sensor configured to in use detect and transmit input data relating to the wearer's motion and/or physiology;

a processor configured to in use process the input data received from the sensor, wherein the processor comprises an algorithm designed to process the input data and generate output data, wherein the output data provides a determination of the motion being performed and/or the physiological state of the wearer, and wherein the algorithm is configurable using input data provided by the sensor and/or a sensor of another wearable device, and wherein the processor is configured to determine whether the algorithm configuration is carried out by the wearable device processor or another processor.

According to yet another aspect of the invention there is provided a wearable device for determining motion of a wearer and/or parameters associated with the motion, the wearable device comprising:

a sensor configured to in use detect and transmit input data relating to a wearer's motion;

a processor configured to in use process the input data received from the sensor, wherein the processor determines the motion being performed by the wearer and/or the parameters associated with the motion.

In a preferred embodiment of the invention, the processor is configured to execute an algorithm to process the input data and generate output data.

The wearable device may be configured to detect, record, process and/or transmit data pertaining to the wearer's motion and/or physiology. The wearer's motion may comprise physical activity including but not limited to exercise type, joint kinematics including joint angle, joint orientations, joint velocity, joint torque, and/or joint acceleration, limb accelerations, limb rotation, limb and/or joint loads, muscle force, muscle strength, and muscle velocity. The wearer's physiological state may comprise physiological parameters including but not limited to electrical activity, temperature, pH, perspiration, heart rate, blood pressure and/or other bio-signals.

The at least one sensor may comprise a rotary encoder, accelerometer, gyroscope and/or magnetometer.

The at least one sensor may additionally or alternatively comprise one or more physiological sensors, including but not limited to a thermometer, electromyography (EMG) sensor, heart rate sensor, blood pressure sensor, and/or blood oxygen level sensor.

The wearable device may be in the form of an orthosis or exoskeleton device. The orthosis or exoskeleton device may comprise a knee, elbow, shoulder, spine or back, ankle and/or wrist brace.

The wearable device may be in the form of a smart watch, smart prosthetic, smart phone, smart shoe or any other suitable 'smart' wearable device comprising a computing device or processor.

The processor may be configured to determine a walking motion and calculate in real-time gait spatiotemporal parameters including but not limited to step length, stride length, and cadence, using biomechanics models and wearer/other user demographics and geometry in real-time.

The output data generated by the processor may provide the determination of the motion being performed and/or the parameters associated with the motion, and wherein the algorithm is configurable using input data provided by the sensor and/or a sensor of another wearable device.

According to yet another aspect of the invention there is provided a method of determining motion and/or a physiological state of a wearer using the wearable device described above and/or a processor.

According to yet another aspect of the invention there is provided a method of configuring the algorithm used to determine motion and/or a physiological state of a wearer using the wearable device described above.

According to yet another aspect of the invention there is provided a method of determining whether process or to in use process the input data received from the sensor is a processor comprised as part of the wearable device processor and/or a processor located remote to the sensor.

According to yet another aspect of the invention there is provided a method of determining whether the re-configuration of the predetermined algorithm is carried out by a processor comprised as part of the wearable device and/or a processor located remote to the sensor.

According to yet another aspect of the invention there is provided a processor-implemented method of determining motion and/or a physiological state of a wearer using the wearable device described above and/or a processor.

According to yet another aspect of the invention there is provided a wearable device for determining a nature of motion and/or a physiological state of a wearer, the wearable device comprising:

a body portion configured to be worn by the wearer; and at least one sensor mounted to the body portion, wherein the at least one sensor is configured to, while the wearable device is being worn:

detect a motion parameter of the wearer and/or a physiological parameter of the wearer; and generate input data indicative of the motion parameter and/or the physiological parameter, the wearable device further comprising:

a processor configured to:

receive the input data from the at least one sensor; and process the input data by executing an algorithm to determine the nature of motion and/or the physiological state of the wearer while the wearable device is being worn.

In examples:

The algorithm comprises one or more steps in which the motion parameter and/or the physiological parameter may be compared to one or more reference parameters.

The algorithm may comprise a support vector machine, random forest or artificial neural network.

The processor is configured to receive training data indicative of the motion parameter and/or the physiological parameter and to configure the algorithm based on the training data.

The training data may be generated by the at least one sensor.

The training data may be received by the processor directly or indirectly from another wearable device, the training data being generated by the other wearable device.

The processor may be configured to receive data indicative of the algorithm from a remote processor.

The processor is configured to determine whether to configure the algorithm based on the training data and/or based on the data indicative of the algorithm from the remote processor.

In examples:

The at least one sensor may comprise at least one motion sensor.

The at least one motion sensor may comprise one or more of: an orientation sensor configured to measure one or more parameters indicative of the orientation of one or more parts of the wearer's body; and a position sensor configured to measure one or more parameters indicative of the relative position of one or more parts of the wearer's body.

The at least one motion sensors may comprise one or more of: a rotary sensor, an accelerometer, a gyroscope and a magnetometer.

The at least one sensor may comprise one or more physiological state sensors.

The one or more physiological state sensors may comprise one or more of: a thermometer, an electromyography (EMG) sensor, a heart rate sensor, a blood pressure sensor, and a blood oxygen level sensor.

In examples:

The wearable device may be a joint brace, wherein the body portion of the joint brace may comprise a first brace portion configured to be mounted in use on one side of a joint of the wearer and a second brace portion configured to be mounted in use on another side of the joint.

A first motion sensor of the at least one motion sensor may be mounted to the first brace portion and a second motion sensor of the at least one motion sensor is mounted to the second brace portion.

A first motion sensor of the at least one motion sensor may be mounted to the first brace portion or the second brace portion, and a second motion sensor of the at least one motion sensor may be mounted to a third brace portion configured to be mounted in use on the joint.

The joint brace may comprise a knee brace, wherein the first brace portion is configured to be mounted in use superior to a knee joint of the wearer and the second brace portion is configured to be mounted in use inferior to the knee joint.

According to yet another aspect of the invention there is provided a system for determining a nature of motion and/or a physiological state of a wearer, the system comprising the wearable device according to any one or more of the previously described aspects and/or examples of the invention.

In examples:

The system may comprise a remote processor located remote from the wearable device and the remote processor is configured to:

receive training data indicative of the motion parameter and/or the physiological parameter from the wearable device;

configure the algorithm based on the training data to generate the configured algorithm; and send data indicative of the configured algorithm to the processor.

The system may further comprise a further wearable device, the further wearable device comprising:

a body portion configured to be worn by the wearer;

at least one sensor mounted to the body portion, wherein the at least one sensor is configured to, while the further wearable device is being worn:

detect a further motion parameter of the wearer and/or a further physiological parameter of the wearer; and generate training data indicative of the further motion parameter and/or the further physiological parameter, the further wearable device further being configured to output the training data to the processor and/or the remote processor.

The remote processor may be configured to:

receive the training data from the further wearable device and the training data from the wearable device, wherein the training data from the further wearable device and the training data from the wearable device are generated while the further wearable device and the wearable device are worn simultaneously by the wearer; and configure the algorithm based on a comparison of the training data from the further wearable device and the training data from the wearable device so that the algorithm is configured, at a future time, to be executed by the processor to determine the nature of motion and/or the physiological state of the wearer based on the input data from the wearable device and without receiving further data from the further wearable device at the future time.

In an example, the processor may be configured to execute the algorithm to determine the nature of motion and/or the physiological state when the further wearable device is not worn by the wearer.

In examples:

The at least one sensor of the further wearable device may comprise at least one motion sensor.

The at least one sensor of the further wearable device may comprise at least one physiological state sensor.

In examples:

The further wearable device may comprise a joint brace, wherein the body portion of the joint brace comprises a first brace portion configured to be mounted in use on one side of a joint of the wearer and a second brace portion configured to be mounted in use on another side of the joint.

The wearable device may be configured to be worn on a wrist of the wearer.

The wearable device may be configured to be worn on a foot of the wearer.

Further aspects of the invention, which should be considered in all its novel aspects, will become apparent to those skilled in the art upon reading of the following description which provides at least one example of a practical application of the invention.

BRIEF DESCRIPTION OF THE DRAWINGS

The invention shall now be described by way of reference to the following non-limiting drawings, in which.

DETAILED DESCRIPTION OF PREFERRED EMBODIMENTS OF THE INVENTION

In an embodiment of the invention there is provided a wearable device for determining a nature of motion and/or a physiological state of a wearer, the wearable device comprising a body portion configured to be worn by the wearer, at least one sensor mounted to the body portion, wherein the at least one sensor is configured to in use detect one or more of a motion event and a physiological event of the wearer and generate input data indicative of the event(s), and a processor configured to receive the input data and determine the motion and/or physiological state of the wearer based on the input data.

The processor is configured to process the input data and generate output data, wherein the output data is indicative of the nature of motion and/or the physiological state of the wearer.

The wearable device may be in the form of a knee, elbow, shoulder, spine or back, wrist and/or ankle orthosis/exoskeleton/brace, smart watch, prosthetic, smart phone, smart shoe or any other suitable computing device. The term “smart shoe” may refer to a wearable device configured to be worn on a foot of the wearer, e.g. a smart insole, shoe or footwear comprising at least one sensor.

Motion/State Determination System

Before describing the features of an exemplary wearable device or steps of how motion and/or a physiological state is determined in more detail there will now be described, with reference to FIG. 1, an exemplary motion/state determination system 300 used in certain forms of the technology for analysis of data provided by the wearable device.

Figure 1:
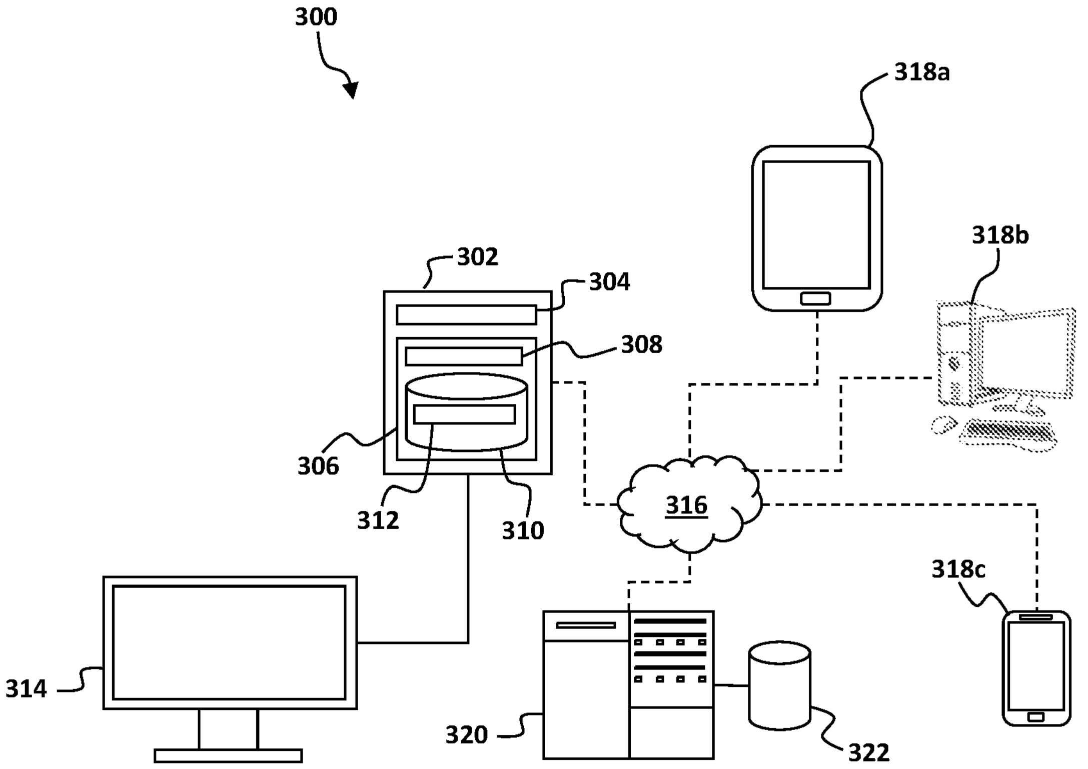
FIG. 1 is a schematic illustration of a processor according to an aspect of the present disclosure.

FIG. 1 is a schematic illustration of a motion/state determination system 300 according to one form of the technology. Motion/state determination system 300 comprises a hardware platform 302 that manages the collection and processing of input data from the one or more sensors which shall be described in more detail below. The hardware platform 302 has a processor 304, memory 306, and other components typically present in such computing devices. The hardware platform 302 may be local to the sensors. In the exemplary form of the technology illustrated the memory 306 stores information accessible by processor 304, the information including instructions that may be executed by the processor 304 and data 310 including output and input data that may be retrieved, manipulated or stored by the processor 304. The memory 306 may be of any suitable means known in the art, capable of storing information in a manner accessible by the processor 304, including a computer-readable medium, or other medium that stores data that may be read with the aid of an electronic device.

The processor 304 may be any suitable device known to a person skilled in the art. Although the processor 304 and memory 306 are illustrated as being within a single unit, it should be appreciated that this is not intended to be limiting, and that the functionality of each as herein described may be performed by multiple processors and memories, that may or may not be remote from each other or from the motion/state determination system 300. The instructions may comprise any set of instructions suitable for execution by the processor 304. For example, the instructions may be stored as computer code on the computer-readable medium. The instructions may be stored in any suitable computer language or format. Data 310 may be retrieved, stored or modified by processor 304 in accordance with the instructions 310. The data 310 may also be formatted in any suitable computer readable format. Again, while the data is illustrated as being contained at a single location, it should be appreciated that this is not intended to be limiting—the data may be stored in multiple memories or locations. The data 310 may also comprise a record 312 of control routines for aspects of the motion/state determination system 300.

The hardware platform 302 may communicate with a display device 314 to display the results of processing of the data. The hardware platform 302 may communicate over a network 316 with user devices (for example, a tablet computer 318*a*, a personal computer 318*b*, a smartphone 318*c*, or a smart watch (not shown)), or one or more server devices 320 having associated memory 322 for the storage and processing of data collected by the local hardware platform 302. It should be appreciated that the server 320 and memory 322 may take any suitable form known in the art, for example a “cloud-based” distributed server architecture. The network 316 may comprise various configurations and protocols including the Internet, intranets, virtual private networks, wide area networks, local networks, private networks using communication protocols proprietary to one or more companies, whether wired or wireless, or a combination thereof.

In order for motion/state determination system 300 to analyse the motion and/or physiological state detected by sensors in order to make a determination, input data is sent from the sensors to the motion/state determination system 300. In some forms, the motion/state determination system 300 may comprise a processor comprised as part of the wearable device. Any suitable data transmission protocol may be used to send the input data, including wired or wireless transmission, and over a communications network, for example the Internet.

Sensors

Exemplary embodiments of the wearable device comprise one or more sensors configured to detect one or more motion/physiological parameter of the wearer and generate input data indicative of the parameter(s). The wearable device in exemplary embodiments may also comprise a processor configured to receive and process the input data from the sensors.

In alternative embodiments the wearable device is configured to transmit input data to a remote processor for processing. The device is configured to detect, record, process and/or transmit data relating to the motion and/or physiological state of the wearer, e.g. an orthosis system or components thereof detects, records, processes and/or transmits data relating to the movement and/or rotation of the orthosis system.

The device may additionally or alternatively detect, record, process and/or transmit data pertaining to the patient's physical activity and/or physiology. This may comprise parameters such as joint kinematics (such as joint angle, joint orientations, joint velocity, joint torque, and/or joint acceleration), limb accelerations, limb rotations, limb and/or joint loads, muscle force, muscle strength, muscle velocity, electrical activity, temperature, pH, perspiration, heart rate, pain, disease, injury, fatigue, stress, anxiety, blood pressure and/or other bio-signals.

In embodiments, the sensor(s) may comprise one or more motion sensors. The motion sensor(s) may comprise one or more of an orientation sensor and a position sensor. For example, the motion sensor(s) may comprise one or more of a rotary sensor, an accelerometer, a gyroscope and a magnetometer. Other motion sensors may comprise optical sensors.

The position sensor(s) may be configured to measure one or more parameters indicative of the relative position of one or more parts of the user's body, for example the position of a first part of the wearer's limb relative to a second part of the user's limb.

The orientation sensor(s) may be configured to measure one or more parameter(s) indicative of the orientation of one or more parts of the user's body, for example the orientation of the wearer's thigh and/or shank.

The sensor(s) may comprise one or more physiological state sensors. For example, the physiological state sensor(s) may comprise one or more of a thermometer, an electromyography (EMG) sensor, a heart rate sensor, a blood pressure sensor, and a blood oxygen level sensor.

The sensor(s) may be configured on one or more sensing modules. In one example, the sensing module(s) may comprise an inertial measurement unit (IMU) which comprises a plurality of motion sensors, e.g. an accelerometer, a gyroscope and a magnetometer. In another example, the sensing module(s) may comprise a rotary sensor.

In embodiments, the wearable device may comprise a transmitter for transmitting input data obtained by or through the sensors to a remote location, for example by RF, Bluetooth, Wi-Fi or any other remote communication protocol.

The sensors may further comprise a receiver configured to receive data remotely from an external source, such as external control signals. Data may be stored or received by the device through a physical data storage device such as a memory card, USB stick or the like.

Other sensors may be provided, comprised in or separate from the wearable device. For example, the wearable device may also comprise one or more torque sensors for detecting joint interaction torque between the patient and a body portion for mounting the sensor(s) to the patient. The torque sensor(s) may be comprised as part of a torque sensing module. For example, such sensor(s) may monitor relative displacement between two or more components of the device, for example between a first brace section and second brace portion. This may enable a torque sensor to sense torque between the first and second brace portions. Torque sensing may be performed when the first and second brace portions are locked, or there is some resistance between them. It should therefore be appreciated that a torque sensing module may also incorporate a locking mechanism to substantially prevent movement (e.g. rotation) between the first and second brace portions, such as described in PCT application PCT/NZ2018/050085.

A person skilled in the art will understand that several sensor types may be suitable for measuring characteristics of a patient's biomechanics. For example, a rotary encoder may be used to measure an angle of displacement between first and second brace portions. Alternatively or additionally an inertial measuring unit(s) (IMU) may be attached to one or each of the first and second brace portions to measure the angle of displacement. An angle of displacement may be used to infer a resistance to motion level, by calibration of a known resistance element with respect to the amount of relative movement between the brace assemblies, or conversely a resistance measurement such as torque or force may be used to infer angle. A strain gauge may be provided to a compliant/resilient element such as a spring or elastomeric block to measure force or torque, and/or a position of a spring element may be used to indicate a resistance to motion level.

In embodiments, the one or more sensors are mounted to a body portion where the body portion is configured to be worn by a wearer. The wearable device may comprise a plurality of body portions.

Joint Brace

In embodiments, the wearable device may be a joint brace, wherein the body portion of the joint brace comprises a first brace portion configured to be mounted in use on one side of a joint of the wearer and a second brace portion configured to be mounted in use on another side of the joint.

In one form, a first motion sensor of the at least one motion sensor may be mounted to the first brace portion and a second motion sensor of the at least one motion sensor is mounted to the second brace portion.

In another form, a first motion sensor of the at least one motion sensor is mounted to the first brace portion or the second brace portion, and a second motion sensor of the at least one motion sensor is mounted to a third brace portion configured to be mounted in use on the joint.

Knee Brace In embodiments, the joint brace comprises a knee brace, wherein the first brace portion is configured to be mounted in use superior to a knee joint of the wearer and the second brace portion is configured to be mounted in use inferior to the knee joint.

Figure 2:
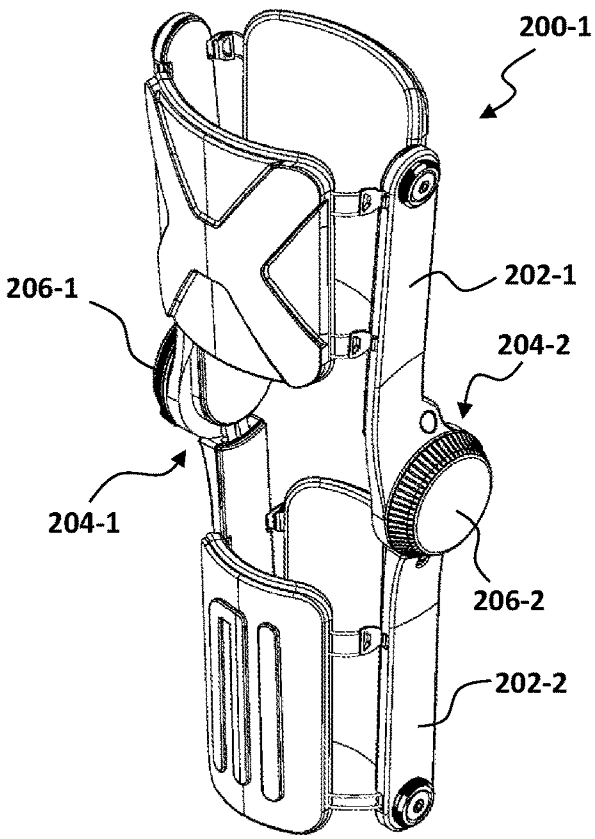
FIG. 2 is a front perspective view of an exemplary wearable device in the form of a knee brace according to an aspect of the present disclosure.

FIG. 2 shows an exemplary wearable device in the form of an orthosis system particularly suited for mounting proximate a knee (not shown) of the patient (not shown)—herein referred to as first knee brace 200-1—as described in PCT Application No. PCT/NZ2018/050085, the contents of which are incorporated herein by reference.

In this embodiment, the knee brace 200-1 comprises a body mounting portion having a first brace portion 202-1 and a second brace portion 202-2. It is to be appreciated that a body mounting portion is an example of the body portion of the wearable device. In use, the first brace portion 202-1 is mounted upwardly of the knee of the patient and the second brace portion 202-2 is mounted downwardly of the knee of the patient.

The first brace portion 202-1 and the second brace portion 202-2 are pivotably coupled via pivot assemblies 204-1 and 204-2. This makes the orthosis system 200-1 suited to use in bracing a pivoting joint of the body, such as the knee.

In other embodiments of the invention the first and second brace portions 202-1, 202-2 are moveably coupled in some other manner, for example through a sliding coupling. Such embodiments may be suitable for use in bracing an extendable part of the body. In yet other embodiments, the brace of an orthosis system may be provided as a flexible sleeve, such as a continuous compression sleeve. A first portion of the sleeve is a first body mounting portion to be worn on one side of the user's joint, and a second portion of the sleeve coupled to (i.e. integrally formed with) the first portion is a second body mounting portion to be worn on an opposite side of the user's joint.

In the embodiment illustrated in FIG. 2, the wearable device 200-1 comprises sensing modules 206-1 and 206-2 which are removably coupled to the pivot assemblies 204-1 and 204-2. One or both of the sensing modules 206-1 and 206-2 may comprise a processor and one or more sensors. While the sensing modules 206-1 and 206-2 are illustrated as being on the sides of the patient's knee, in other embodiments the orthosis system may be configured to mount sensing modules in other positions in relation to the body.

Figure 3:
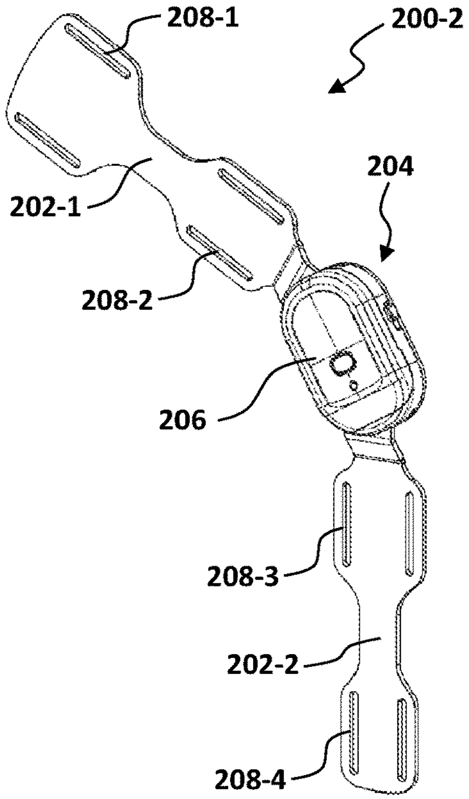
FIG. 3 is a front perspective view of another exemplary wearable device in the form of a knee brace, wherein only one side of the knee brace is shown.

FIG. 3 shows an embodiment of a knee brace 200-2 according to another aspect of the technology. Knee brace 200-2 comprises a body mounting portion having a first brace portion 202-1 and a second brace portion 202-2. In use, the first brace portion 202-1 is mounted upwardly of the knee of the patient and the second brace portion 202-2 is mounted downwardly of the knee of the patient. In this exemplary embodiment, the brace portions 202 comprise stiff arms (for example made of aluminium) having strap mounting features (for example slots 208-1, 208-2, 208-3, 208-4) for positioning flexible straps (not illustrated) for mounting the knee brace 200-2 to a user.

In this embodiment, a sensing module 206 is removably coupled to the pivot assembly 204 of the knee brace 200-2. The sensor module 206 comprises a rotational knee movement sensor, and an IMU for sensing thigh movement.

Elbow Brace

Figure 4:
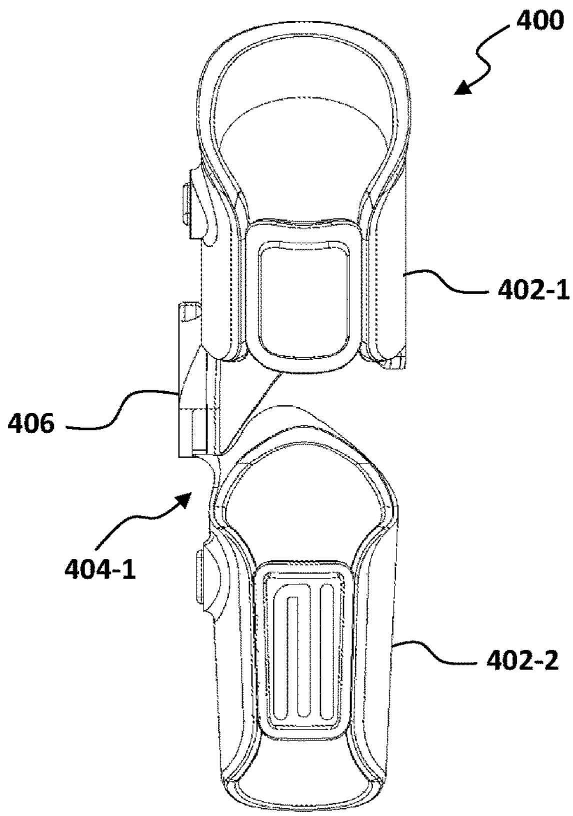
FIG. 4 is a front view of an exemplary wearable device in the form of an elbow brace according to an aspect of the present disclosure.

FIG. 4 shows an exemplary wearable device particularly suited for mounting proximate an elbow (not shown) of the patient (not shown)—referred to herein as elbow brace 400—as described in PCT Application No. PCT/NZ2018/050085, the contents of which are incorporated herein by reference.

It will be noted that the body mounting portion in this embodiment comprises a first brace portion 402-1 configured to wrap around a first portion of the patient's arm. Similarly, the second brace portion 402-2 is configured to wrap around another portion of the patient's arm.

The first brace portion 402-1 and the second brace portion 402-2 are pivotably coupled via pivot assembly 404-1, to which a sensor module 406 is mounted, the sensing module 406 including a processor and one or more sensors.

Spine or Back Brace

Figure 4A:
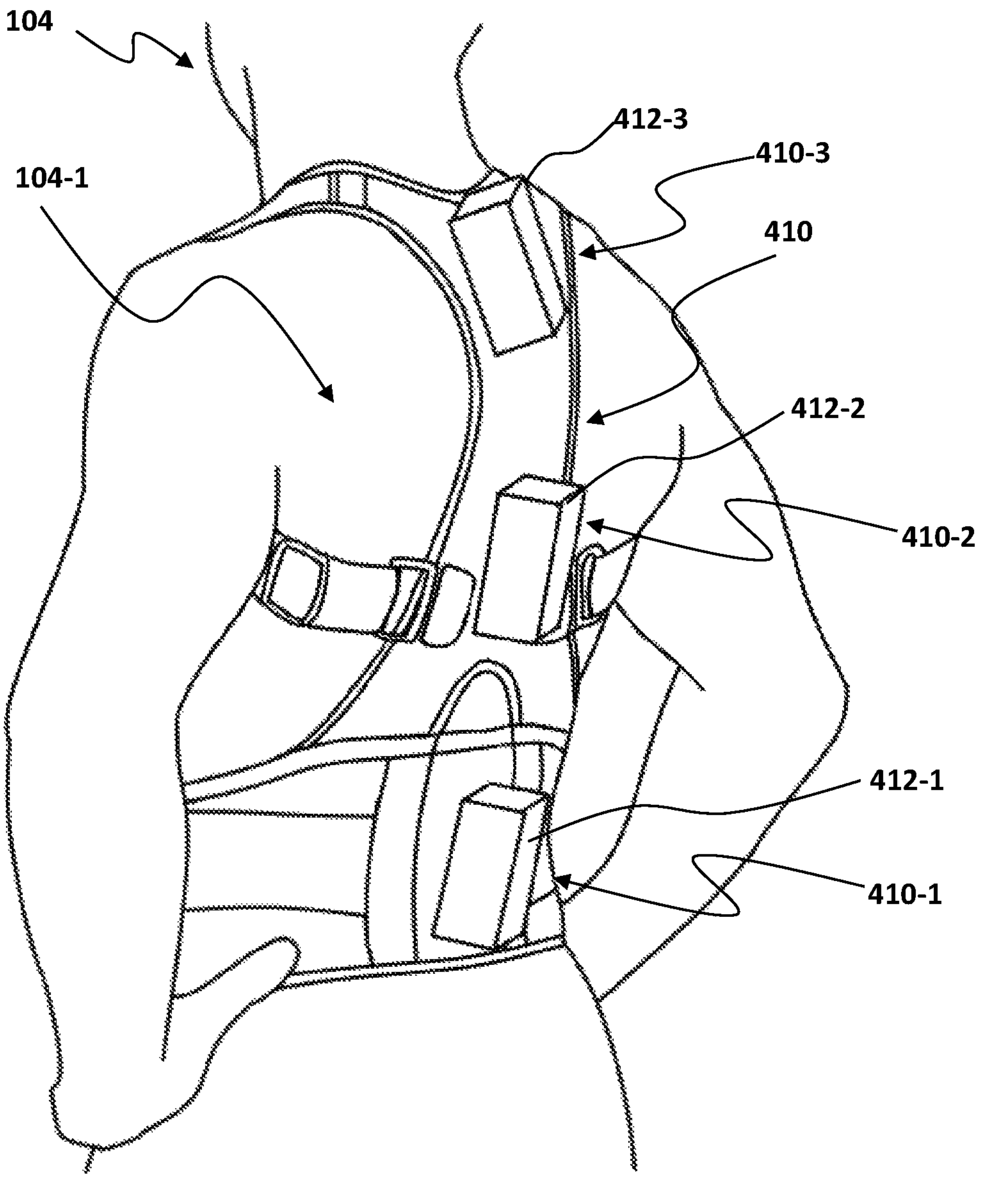
FIG. 4A is a representation of an exemplary wearable device in the form a back brace according to an aspect of the present disclosure.

In an embodiment of the present invention illustrated in the FIG. 4A, the wearable device is in the form of a spine or back brace 410. The body portion of the back brace 410 is mounted to the patient 104 in the region of the patient's back 104-1. The sensors on-board the back brace 410 may detect input data relating to kinematics and/or shape deformation of a patient's spine and transmit it to the on-board processor and/or remote processer. The processor may be configured to generate output data, wherein the output data provides a determination relating to the patient's posture, e.g. good or bad posture, and/or a determination relating to spinal or back motion/activity, e.g. sitting, slouching, bending over.

As illustrated, the back brace 410 may comprise one or more sensor modules 412-1, 412-2, 412-3. The sensor modules 412-1, 412-2, 412-3 may be configured to measure the position and/or orientation of one or more parts of the patient's back 104-1. The input data generated by the sensor(s) is indicative of the position and/or orientation of the parts of the back or spine.

FIG. 4A shows the sensor modules 412-1, 412-2, 412-3 positioned on different regions of the patient's back 104-1. This facilitates the measurement of the position/orientation of these different regions in order to determine a spinal or back motion/activity and/or the patient's posture. As shown, a first sensor module 412-1 is mounted to a first brace portion 410-1 and located in use in an inferior medial region of the back 104-1. A second sensor 412-2 module is mounted to second brace portion 410-2 and located in use in a central medial region of the back 104-1. A third sensor module 412-3 is mounted to a third brace portion 410-3 and located in use in a superior medial region of the back 104. In the illustrated example, each of the sensor modules 412-1, 412-2, 412-3 comprises an IMU.

Another Embodiment of the Motion/State Determination System

Figure 5:
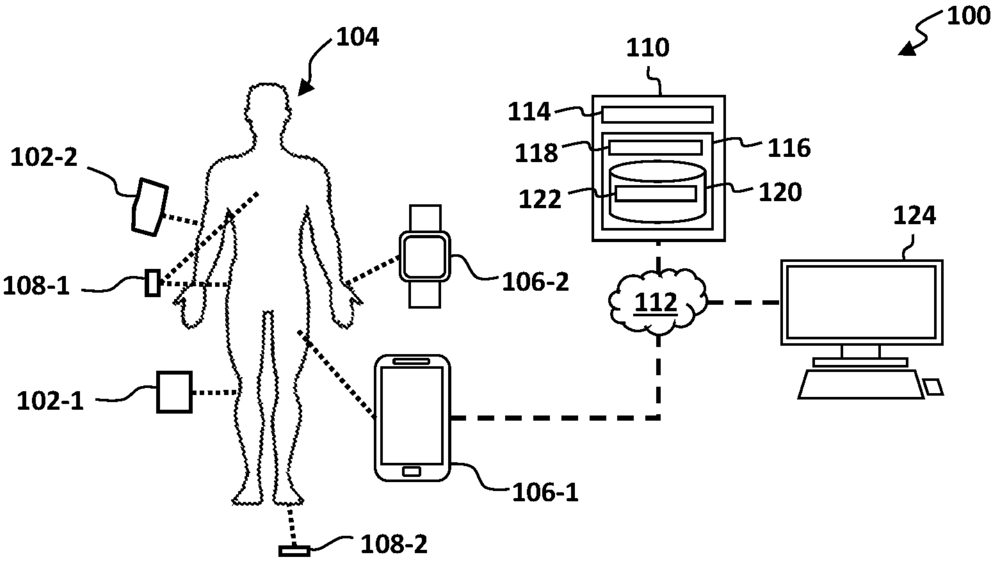
FIG. 5 is a schematic diagram showing features of a symmetry analysis system according to an aspect of the present disclosure.

FIG. 5 is a schematic showing features of a motion/state determination system 100 according to another embodiment of the invention.

The system 100 comprises one or more wearable devices 102 (for example, knee orthosis 102-1 and/or elbow orthosis 102-2) configured to be mounted to a corresponding body part (s) of a body of a patient 104 in use. At least one of the wearable devices illustrated is a wearable device according to an aspect of the present disclosure, wherein the at least one wearable device comprises one or more sensors and a processor, as described herein.

The system 100 further comprises one or more reference sensors, including intelligent user devices 106 (for example, smart phone 106-1 and/or smart watch 106-2, and/or smart shoe which is not shown) and/or dedicated reference sensor devices 108 (for example, an inertial measurement unit (IMU) 108-1 and/or smart insole 108-2). The intelligent user devices 106 and dedicated reference sensor devices 108 may take the form of, or be comprised as part of, a further wearable device.

In exemplary embodiments, data from one or more of the wearable devices 102, user devices 106, and/or reference sensor device 108 may be communicated to a remote processor or processing system 110 via a network 112 (for example a cellular network, or another network potentially comprising various configurations and protocols including the Internet, intranets, virtual private networks, wide area networks, local networks, private networks using communication protocols proprietary to one or more companies—whether wired or wireless, or a combination thereof). For example, the smart phone 106-1 may operate an application capable of interfacing with the remote processing system 110.

The remote processor or processing system 110 may be configured to receive training data indicative of the motion parameter and/or the physiological parameter from the wearable device, configure the algorithm based on the training data to generate the configured algorithm, and send data indicative of the configured algorithm to the processor of the wearable device.

Among other functions, the remote processing system 110 may record data, perform analysis on the received data, and report to one or more user devices. In this exemplary embodiment, the remote processing system 110 is illustrated as being implemented in a server—for example one or more dedicated server devices, or a cloud-based server architecture. By way of example, cloud servers implementing the remote processing system 110 may have processing facilities represented by processors 114, memory 116, and other components typically present in such computing environments. In the exemplary embodiment illustrated the memory 116 stores information accessible by processors 114, the information including instructions 118 that may be executed by the processors 114 and data 120 that may be retrieved, manipulated or stored by the processors 114. The memory 116 may be of any suitable means known in the art, capable of storing information in a manner accessible by the processors, including a computer-readable medium, or other medium that stores data that may be read with the aid of an electronic device. The processors 114 may be any suitable device known to a person skilled in the art. Although the processors 114 and memory 116 are illustrated as being within a single unit, it should be appreciated that this is not intended to be limiting, and that the functionality of each as herein described may be performed by multiple processors and memories, that may or may not be remote from each other.

The instructions 118 may comprise any set of instructions suitable for execution by the processors 114. For example, the instructions 118 may be stored as computer code on the computer-readable medium. The instructions may be stored in any suitable computer language or format. Data 120 may be retrieved, stored or modified by processors 114 in accordance with the instructions 118. The data 120 may also be formatted in any suitable computer readable format. Again, while the data is illustrated as being contained at a single location, it should be appreciated that this is not intended to be limiting—the data may be stored in multiple memories or locations. The data 120 may comprise databases 122 storing data such as historical data associated with one or more of the one or more of the wearable devices 102, user devices 106, and/or reference sensor devices 108, and the results of analysis of same.

It should be appreciated that in exemplary embodiments the functionality of the remote processing system 110 may be realized in a local application (for example, on smart phone 106-1, or another personal computing device 124), or a combination of local and remote applications. Further, it should be appreciated that data may be transferred from one or more of the devices by other means—for example wired communication links or transfer of storage devices such as memory cards.

The results of analysis, and/or underlying data, may be displayed on any suitable display device—for example smart phone 106-1, or computing device 124.

In exemplary embodiments, determination of the indicator of symmetry and/or symmetry may be performed by one or more of at least: dedicated processor(s) of the wearable device, processor(s) of a device including a reference sensor, processor(s) of a user device (for example, a personal computing device such as a smart phone, tablet, or personal computer), and remote processing means (for example, a server or cloud computing services). The various components described herein may communicate using any suitable means known to those skilled in the art of data communication, including wired and wireless communication protocols. In exemplary embodiments, data from the wearable device and/or reference sensor may be stored locally (e.g. on removable memory device) and transferred by physical removal of the storage device. Display of a determination of symmetry, and in exemplary embodiments the underlying data, may be displayed on any suitable display device.

Determination of Motion and/or a Physiological State of Wearer

In certain forms of the invention the wearable device comprises a processor configured to receive the input data from the at least one sensor, and process the input data by executing an algorithm to determine the nature of motion and/or the physiological state of the wearer while the wearable device is being worn.

The algorithm may comprise one or more steps in which the motion parameter and/or the physiological parameter detected by the at least one sensor may be compared to one or more reference parameters. The reference parameters may comprise predefined threshold parameters. The reference parameters may comprise parameters defined as part of a process of configuring the algorithm based on the training data. The configuration of the algorithm will be explained in more detail below.

Figure 6:
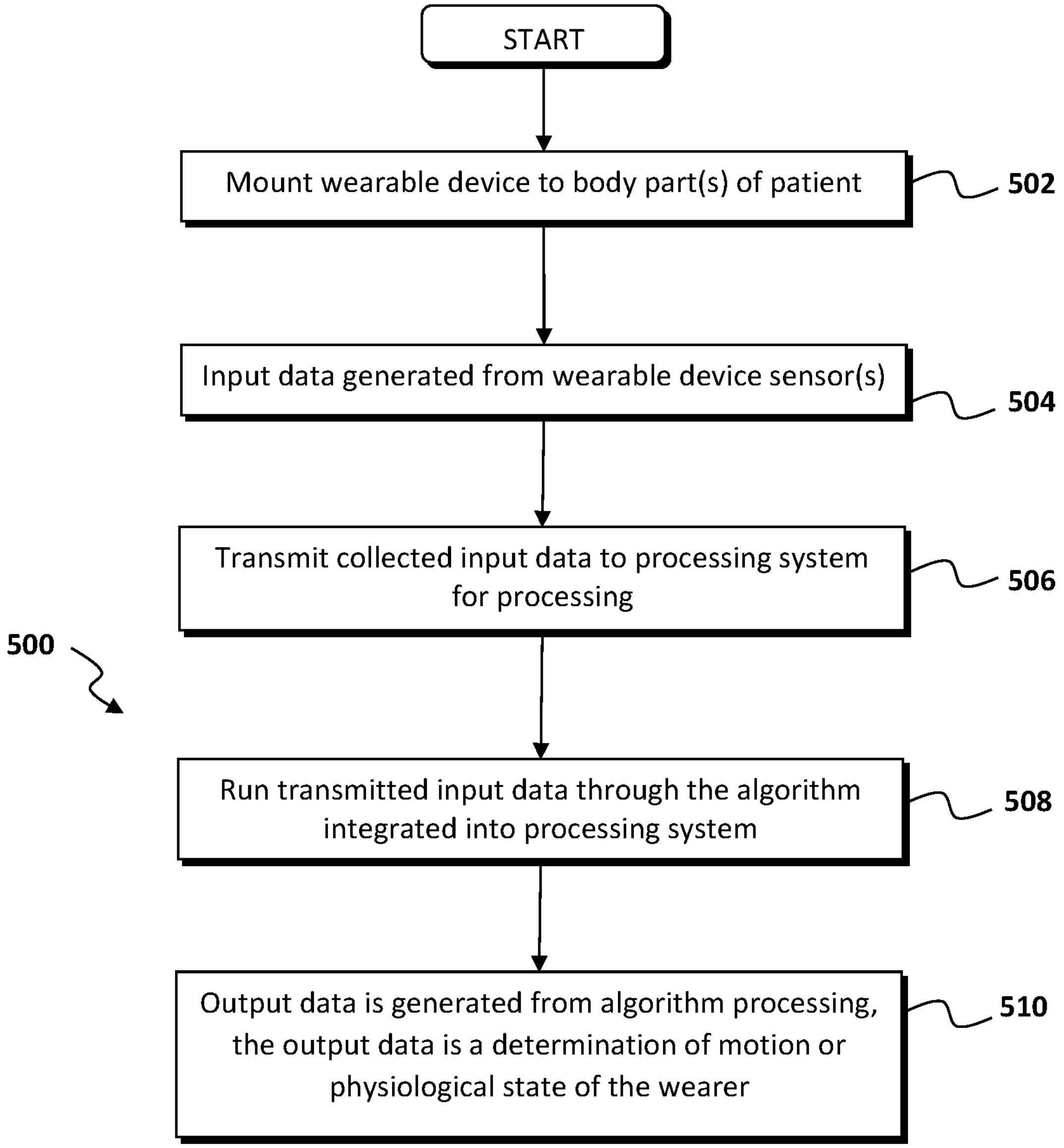
FIG. 6 is a flow chart illustrating determination of motion and/or physiological state of the wearer according to an aspect of the present disclosure.

FIG. 6 illustrates a method 500 of determining the motion of a wearer using the wearable device described herein. An example of implementation of the method 500 shown in FIG. 6 will be described with reference to the use of the exemplary wearable device shown in FIG. 2.

In a first step 502, a wearable device 204-1 including body mounting portion 204-1, 204-2 and sensing module 206-1 is mounted to a first leg of the wearer (not shown).

In a second step 504, input data is generated by the sensor of sensing module 206-1 during activity by the wearer. By way of example, the activity may be a performance of a specific task—such as a hop test, or a walk test over a designated distance—or general activity of the wearer. The input data may be data representative of movement of the device (and therefore the user's leg), for example the relative angle of the first and second brace portions 202-1, 202-2 over time, accelerometer data, IMU data, etc.

In a third step 506, the input data collected by the sensor is sent to the processor which, may be comprised in the sensing module 206-1 of the wearable device, or may be a remote processor. The input data may comprise data relating to multiple motion events where sensors are configured to detect and generate input data relating to multiple motion events. The sensor may be configured to detect and generate input data relating to a first motion event, and/or a second motion event and repetition of the first motion and/or second event to indicate a motion cycle. Additionally or alternatively, the sensors may be configured to generate input data relating to orientation of body parts relative to each other, and/or the distance between body parts. Additionally or alternatively, the sensors may be configured to generate input data relating to velocity of the motion and/or other parameters of the motion.

In a fourth step 508, the transmitted input data is processed by the processor, for example by being subject to an algorithm that the processor is configured to run. The input data relating to multiple motion events may be used to determine multiple motion events. The algorithm may comprise a set of instructions which are performed in sequence by the processor. The set of instructions may comprise instructions to detect, calculate and/or aggregate input data relating to multiple motion events. For example, algorithm instructions may comprise one or more of the following:

detect at least one motion event using at least one sensor;
detect a repeat of the at least one motion event to indicate completion of a motion cycle;
calculate orientation of moving body parts relative to each other;
calculate an angle between joints and/or distance between moving body parts relative to each other;
calculate velocity of motion event;
calculate parameters of motion event; and
aggregate data relating to the above.

The algorithm may be configured to detect and/or calculate one or more parameters by way of detecting and/or calculating an event.

In a fifth step 510, output data is generated as a result of the processing performed by the processor (for example, the algorithm), wherein the output data comprises a determination of motion or physiological state of the wearer. For example, the output data may be generated by execution of the above described instructions, wherein the output data provides a determination or indication of the motion, activity and/or physiological state of the wearer.

Input Data Processing

In an embodiment of the invention the processor 114, 304 may be configured to execute an algorithm designed to process the input data and determine the motion being performed and/or the physiological state of the wearer.

The algorithm may comprise a predetermined sequence of instructions, series of steps or a set of rules for computing on the processor. Computing may comprise calculating and/or data processing. The instructions, steps or rules of the algorithm may be executed on the processor 114, 304 such that the input data which relates to the motion and/or physiological state of the wearer and which is collected using the sensor(s) may be used to determine the nature of the motion and/or physiological state of the wearer.

In preferred forms, the algorithm may be executed on the processor 304 comprised as part of the wearable device e.g. device 102-1. Alternatively, the algorithm may be executed remotely on a remote processor 114 or cloud server system.

The algorithm may be implemented through a computer program pre-programmed or otherwise executed using the processor. It is to be appreciated that the term algorithm is, unless the context clearly indicates otherwise, intended to be construed broadly to mean any process or series of steps involving calculations and other operations that may be undertaken by the processor, and comprises any of the types of algorithm referred to in examples in this specification.

The processor may be configured to configure the algorithm using machine learning techniques, for example to identify parameters of the wearer and his/her motion and/or physiological state and update the algorithm model accordingly.

The algorithm may be a rule-based or threshold-based analytical model. The model may comprise a subset of parameters which may be configured to define the model behaviour, i.e. threshold parameters. In some embodiments the algorithm may comprise a conventional motion and/or physiological state determination algorithm where the parameters may relate to motion and/or physiological state. In embodiments, the subset of parameters may be updated using machine learning techniques.

The processor may be configured such that the output data generated by the algorithm which provides a determination of the nature of the motion being performed and/or the physiological state of the wearer includes but is not limited to activity (type and quality e.g. walking and speed, limp or squats and knee angle bend), fatigue, ability, disability, disease, injury, stress, pain, capability, and exertion etc.

The processor may be configured such that the output data generated may also determine whether the wearable device, e.g. orthosis such as a knee, elbow or ankle brace, is being worn or not by the wearer. This determination may be made when no input data received by the processor from the sensor(s).

Exemplary Determination Algorithms

In certain embodiments of the invention, the wearable device 204-1, 102-1 may be configured to determine the nature of the motion of the wearer as being walking, hopping or squatting.

Determination of Walking

In an embodiment of the invention, the wearable device 204-1, 102-1 may be configured to determine that the wearer is walking, and may be additionally or alternatively configured to determine the type of walking, i.e. the gait of the wearer. The sensors may be configured to detect one or more gait parameters and generated input indicative of the parameters, e.g. gait spatiotemporal parameters including but not limited to step length, stride length, and cadence.

In some forms, the sensor(s) may be configured to detect a first gait event, e.g. heel strike, and a second gait event, e.g. toe-off event. In an example, the first gait event is detected by an IMU. For example, the sensor(s) generate input data which is an acceleration parameter which is indicative of a heel strike and/or toe off event.

The sensor(s) may be configured to measure functional range-of-motion. For example, the sensor(s) may be configured to measure a maximum joint angle and a minimum joint angle during an activity performed by the user, e.g. walking. For example, one or more of the sensor arrangements described herein may be configured to measure the maximum and minimum joint angles of the knee. In one example, the knee orthosis/brace comprises first and second sensor modules, e.g. IMUs, located in use above and below the knee joint. In another example, the knee orthosis/brace comprises a first sensor module, e.g. rotary sensor, located in use above or below the knee joint, and a second sensor module, e.g. rotary sensor, located in use on the knee joint.

The processor may be configured to receive the input data from the sensor(s) and process it to determine walking and/or gait. For example, the processor may be configured to execute a kinematic equation to calculate hip over ground motion using joint angles and a user's limb lengths to determine the gait parameter(s), e.g. over ground speed, stride length and stride time.

In certain forms, the processor may be configured to process the input data and determine the gait of the wearer by execution of an algorithm, wherein the algorithm may comprise a set of instructions configured to cause the processor to:

(a) detect a first event, e.g. heel strike event based on the accelerometer input data received from the IMU;
(b) detect a second event, e.g. toe off event based on the accelerometer input data received from the IMU;
(c) detect repeat of first event, e.g. next heel strike based on the accelerometer input data received from the IMU. This may determine a stride has been completed. The processor may determine a walking motion based on this. In an example, the next heel strike should be detected within a predetermined period of time.
(d) calculate distance travelled in stance phase, e.g. calculate horizontal and vertical distance of the ankle to the hip at the first gait event and at the second gait event. In an example, this is calculated using predefined dimensions of the thigh and shank and orientation of the thigh and shank which may be measured by one or more of the IMU(s) and rotary sensor;
(e) calculate walking velocity. In an example, this is calculated by using the distance in stance phase and the timing of the first and second events;

(f) calculate the distance travelled in the swing phase. In an example, this is calculated by extrapolating/relating/scaling the walking velocity in stance phase to time in swing phase;

(g) calculate total distance on each step. In an example, this is calculated by adding the distance in stance phase with the distance in swing phase;

(h) determine the functional range-of-motion, e.g. determine the maximum joint angle(s) and minimum joint angle(s) during the gait cycle; and (i) collect and/or aggregate data over multiple gait cycles. In an example, this may be done by performing a predetermined number of steps and/or it may be done over a predetermined period of time, e.g. 5 min of walking.

Determination of Hopping

In an embodiment of the invention, the wearable device 204-1, 102-1, the wearable device may be configured to determine a hopping motion of the wearer. The sensor(s) may be configured to detect one or more hopping motion parameters and generate input data indicative of the parameters.

The processor may be configured to process the input data and determine hopping by execution of an algorithm, wherein the algorithm may comprise a set of instructions configured to cause the processor to:

(a) detect a first event, e.g. foot strike event based on the accelerometer input data received from the IMU;

(b) detect a second event, e.g. lift-off event based on the accelerometer input data received from the IMU. In an example, this step is optional;

(c) detect repeat of first event, e.g. next foot strike based on the accelerometer input data received from the IMU. This may determine a hop has been completed. The processor may determine a hopping motion based on this. In an example, the next foot strike should be detected within a predetermined period of time;

(d) calculate distance in stance phase, e.g. calculate horizontal and vertical distance of the ankle to the hip at the first hop event and at the second hop event. In an example, this is calculated using predefined dimensions of the thigh and shank and orientation of the thigh and shank which may be measured by one or more of the IMU(s) and rotary sensor;

(e) calculate hop velocity. In an example, this is calculated by using the distance travelled in stance phase and the timing of the first and second events;

(f) calculate the distance travelled in the jump/hop phase. In an example, this is calculated by extrapolating/relating/scaling the hop velocity in stance phase to time in jump/hop phase;

(g) calculate total distance on each hop. In an example, this is calculated by adding the distance in stance phase with the distance in jump/hop phase;

(h) determine the functional range-of-motion, e.g. determine maximum knee joint angle(s) and minimum knee joint angle(s) during the hop cycle;

(i) determine the knee joint angle at one or more of the first and second events; and (j) collect and/or aggregate data over multiple hop cycles. In an example, this may be done over a predetermined period of time and/or by performing a predetermined number of hops, e.g. 10 hops.

Determination of Squatting

In an embodiment, the wearable device, e.g. knee brace 200-1, 200-2 may be configured to determine a squatting motion of the wearer. The sensor(s) may be configured to detect one or more squatting motion parameters and generate input data indicative of the parameters.

The processor may be configured to process the input data and determine squatting by execution of an algorithm, wherein the algorithm may comprise a set of instructions configured to cause the processor to:

(a) detect a first event, e.g. upright position. In an example, when the thigh and shank are orientated substantially vertical, the wearer is in the upright position. This may be calculated by measuring orientations of the thigh and shank using one or more of the IMU(s) and rotary sensor;

(b) detect a second event, e.g. squat position. In an example, this is calculated by measuring parameters indicative of the orientation of the thigh and/or shank and comparing the parameters to one or more predefined parameters indicative of the orientation of the thigh and/or shank to determine whether the wearer is in the squat position;

(c) detect repeat of first event, e.g. next upright position. This may determine a squat has been completed;

(d) calculate the velocity of the knee joint. This may determine a change in direction of the knee joint which is indicative that the wearer is in the squat position. This step may be optional;

(e) determine the functional range-of-motion, e.g. maximum knee joint angle(s) and minimum knee joint angle(s) during the squat cycle;

(f) determine the knee joint angle at one or more of the first and second squat events, e.g. lowest point in squat; and (g) collect and/or aggregate data over multiple squat cycles. In an example, this may be done over a predetermined period of time and/or by performing a predetermined number of squats, e.g. 10 squats.

Other Artificial Intelligence

In an embodiment of the invention, the processor (remote processor 114 and/or on-board processor 304) may be configured with an artificial intelligence (AI) system or model including but not limited to an artificial neural network (ANN) and/or machine learning or other AI system or model known to persons skilled in the art, i.e. other than the rule-based algorithmic methods described above. The AI system or model is configured to process the input data and determine the nature of the motion being performed and/or the physiological state of the wearer. The AI system or model may be configured or trained with appropriate training data in a prior step, as will be described in more detail below. In examples, the AI system or model may comprise a random forest, support vector machine (SVM), Markov models, convolutional neural network (CNN), recurrent neural network (RNN), or other suitable AI system or model or type of ANN known to persons skilled in the art.

In embodiments, an AI model-based algorithm executed by the processor on the wearable device may comprise a support vector machine, random forest or artificial neural network.

In embodiments, the AI model-based algorithm may be designed or structured prior to implementation and operation on the wearable device's on-board processor. The AI system may be designed so that it is suitable for operation on-board the wearable device.

The algorithm may be designed to make determinations quickly, e.g. in real-time or near real-time, i.e. with a processing time that is less than a predetermined processing time threshold that is desired. The algorithm may also be configured to make determinations accurately, e.g. with an accuracy that is more than a predetermined accuracy threshold that is desired. The processor's memory, e.g. Random Access Memory (RAM), and speed may be a constraint on the size, design or structure of the AI model-based algorithm. The processor may also need to be sufficiently physically small enough in order to fit and operate on the wearable device without being too obtrusive, large and/or heavy. A suitable size will vary depending on where on the body the wearable device is used, and the form factor of the device, as will be apparent to the skilled addressee.

The number of motions/states, e.g. activities, that may be determined by the processor in a predefined amount of time with a predefined accuracy may also be a constraint on the size/design/structure of the AI model. For example, the AI model may need to be configured to determine a predefined group of motions within one second of the motions being completed with 95% accuracy.

The AI model may be designed or structured to meet requirements based on the application for that wearable device, e.g. for gait, hopping, and/or squatting determination. Other requirements may comprise the size and weight of the wearable device, and/or power consumption of the wearable device. These and other factors as described above, define what processor may be used for wearable device for a certain application. For example, a wearable device in the form of a smart watch may be physically smaller than a knee brace, therefore have a smaller processor.

Processing input data offline or remotely from the wearable device may assist in removing (or reducing) constraints on the size/specification of the processor, and therefore this type of AI model may not require designing or structuring. However, when processing the input data on-board the wearable device (i.e. in a processor comprised as part of the wearable device), the size of the processor is restricted as well as the application requirements for the wearable device e.g. real-time predictions or determinations.

The AI model may be designed or configured based on the requirements/constraints discussed above. The design process may involve starting with a large complex model and evaluate this against the requirements. If the model is too large, the number of inputs or features (discussed below) may need to be reduced, for example the number of layers in the ANN may need to be reduced, until the model meets the requirements.

The AI model may be designed/structured to maximise the accuracy of the model for the given constraints such as size of the processor, or at least provide a high level of accuracy.

The AI model is configured to create a model structure based on the inputs, features and model size/structure that fits on the processor.

Referring again to the requirements based on the application of the wearable device, when designing the AI model, the types of activities and/or how many activities the wearable device should detect are considered, e.g. walking and running, or walking, running, sitting, jumping, squats, and lunges. This applies to the accuracy of the determination made by the wearable device. For example, the AI model to be implemented on a consumer device may have a lower accuracy than a medical device, e.g. 90% accuracy may be considered suitable for a consumer device, but for a medical device, 98% may be considered necessary. Therefore when designing the AI model, the accuracy may be considered. This also extends to processing speed. For example, if the application is for an in-person synchronous examination then the AI model may need to make near real-time determinations, e.g. within three seconds. On the other hand, the requirement may be "a store and forward" system, e.g. a health care practitioner such as a physiotherapist or doctor reviews the output data generated by the AI model at a later point in time. In this example, the processor may not need to make determinations in near real-time, and there may be a longer determination time, e.g. 30 seconds.

In examples, the AI model structure/design may need to be determined before implementation and operation on the processor. Once designed, the AI model, e.g. the algorithm, may be configured using training data, as described in the specification.

AI model design may be an iterative process. The iterations may be done manually or with a local or global optimisation algorithm, e.g. genetic algorithms or gradient descent approach.

In certain form, the following factors or requirements may be used to design/structure the AI model:

Input Data from Sensors

- This may comprise defining a window size for feature selection, i.e. defining the number of samples in a software-implemented buffer used to calculate the features. This may comprise defining a type of window, e.g. a sliding window, overlapping window, and/or variable window size. This may comprise defining and applying a time constraint to limit the number of samples, to define the window size.
- This may comprise defining what sensor signals to use, i.e. defining sensor input data that may be more useful than other sensor input data. The number or amount of input data, e.g. sensor signals may be reduced to reduce the AI model size and the increase processing speed.

Feature identification

- This may comprise defining time series data or frequency domain to extract features for use in the AI algorithm, e.g. minimum, maximum, Root-Mean-Square, mean, median interquartile range etc. More features may result in a larger AI model and more processing time.
- This may comprise applying a deep learning approach where no features are necessary to be identified. This may tend to increase the size of the AI model.

Model structure

- This may comprise defining the hyper parameters. This may comprise defining the number of trees in a random forest, number of layers in a NN, or the type of kernel function in a support vector machine.

Implementation in code

- This may comprise defining the format and structure of sensor buffers. This may comprise quantization to reduce the bit precision.
- This may comprise implementation of the AI model into lower-level code, e.g. embedded c code, or machine code.

Output layer and evaluation

- This may comprise defining the evaluation method used to evaluate and train the AI model, e.g. confusion matrix, repeated k-fold cross validation or other performance metrics such as true positives and true negatives or total classifications.
- This may be done on the wearable device or off-line and parameters uploaded to the wearable device.
- This may comprise defining whether the model needs to be trained for different people, or for the same person as they recover.

Determination of Repetitions

In an example, the processor is configured to execute an algorithm to determine or count the repetitions of one or more motions and/or states.

The processor may be configured to count the repetition by applying an algorithm. In an example, the algorithm may be configured to detect one or more parameters indicative of a repetition in a cyclic movement. For example, a peak or trough in an acceleration parameter sensed by an accelerometer may be detected. In another example, a zero crossing may be detected, e.g. the zero crossing of velocity, differential joint angle or limb motion detected during the motion/activity. The repetition count is calculated based on the parameters detected.

In combination with the determination of the type of motion, such as described above, the processor may therefore be configured to number of movements of the determined motion performed by the wearer, i.e. the repetition count.

Algorithm Configuration

In an embodiment of the invention, the processor 304, 114 may be configured to receive training data indicative of the motion parameter and/or the physiological parameter detected by the at least one sensor of the wearable device, and to configure the algorithm based on the training data. Reference to training data in this description may refer to data that has been labelled, i.e. input data with a label. For example, input data generated by the at least one sensor of one or more wearable devices that has been labelled with an output label. Training data and the collection of training data shall be described in more detail below.

In embodiments, the training data may be generated by the at least one sensor of the wearable device, as described in more detail below. In other embodiments, the training data may be received by the processor directly or indirectly from another wearable device. The training data may be generated by the other wearable device. For example, the input data indicative of the motion/state parameters which is generated by at least one sensor of the other wearable device may be labelled with an output label to provide the training data then used to configure the algorithm.

The parameters of the algorithm model may be defined by the completion of a configuration step. Configuration may use a set of input data with a predefined output label to define the parameters of the algorithm model. Configuration can be carried out by many means known to those skilled in the art, including gradient descent or global optimisation, and may be dependent on the type of algorithm model used.

Figure 7:
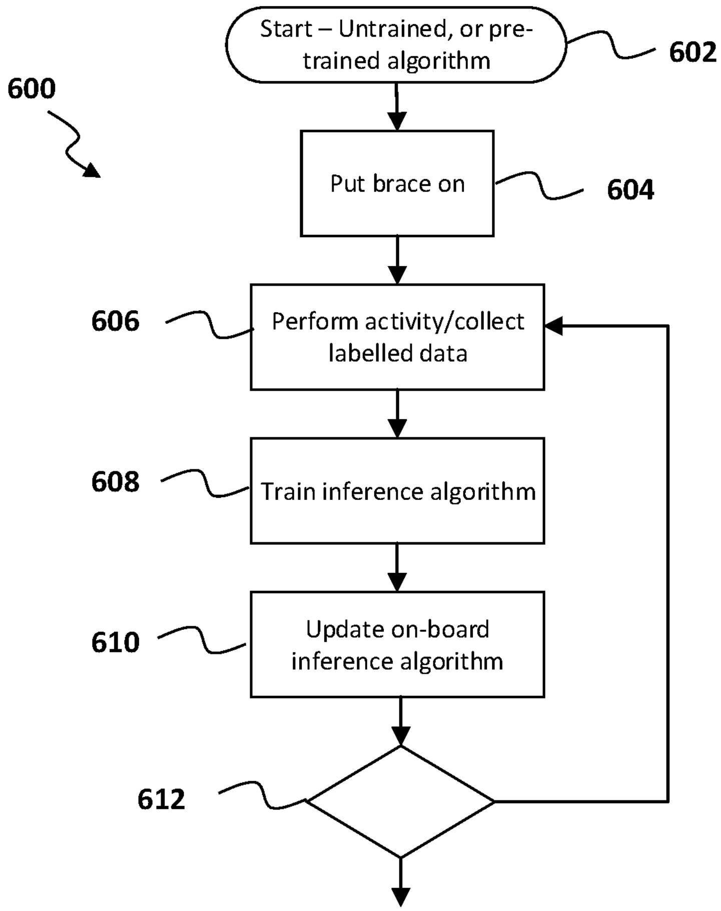
FIG. 7 is a flow chart illustrating configuration of an algorithm of the processor according to an aspect of the present disclosure.

FIG. 7 illustrates a method of configuring the algorithm used to determine motion and/or a physiological state of a wearer using the wearable device described herein. An example of implementation of the method 600 shown in FIG. 7 will be described with reference to the use of the exemplary wearable device shown in FIG. 2.

In a first step 602, the processor of the knee brace 204-1, or the processor of a remote processing system configured to receive data from the knee brace 204-1, is pre-programmed to execute a pre-configured algorithm, e.g. the algorithm is pre-trained or configured before being loaded onto the processor of the knee brace 204-1 or remote system.

In a second step 604, a knee brace 204-1 including body mounting portion 204-1, 204-2 and sensing module 206-1 is mounted to a first leg of the wearer (not shown).

In a third step 606, the wearer performs an activity such as walking while wearing the knee brace 204-1 such that input data is collected by the sensors and this input data is labelled and sent to the processor. Performance of the activity may be prompted, or input data collection may occur automatically upon first use, e.g. when the wearer first walks with the brace on. Other ways of collecting and labelling the input data as described in more detail below, may be performed in step 606.

In a fourth step 608, the labelled input data configures or trains the algorithm, such as described herein.

In a fifth step 610, the algorithm configured to be executed by the processor on-board the knee brace 204-1 or by the remote system is updated.

In a sixth step 612, the algorithm may be configured or trained periodically or continuously wherein the steps of 606 to 610 are repeated. Additionally or alternatively, further configuration or training may be prompted manually or triggered and carried out in one or more of the ways described herein.

Configuration Using Pre-Loaded Data

Configuring the algorithm may comprise defining the parameters of the algorithm model using input data which is collected from a test wearer or group of test wearers which excludes the wearer himself/herself. In this example, configuration of the algorithm may be carried out remotely on processor 114, e.g. the algorithm model parameters are pre-determined and pre-loaded onto the processor 304 of a wearable device e.g. device 106-2 before use by the wearer.

The algorithm may be configured or trained using training data which may be collected from a person or people performing a motion and/or in a physiological state using one or more sensors. In examples, a group of people perform an activity, e.g. squatting, multiple times. Input data is generated by the sensor(s) on a wearable device/system used by each person in the group when performing the activity. The input data generated during this activity is labelled, e.g. as "squatting", to provide the training data. The trained data may be used to configure or train the algorithm. This configured or trained algorithm may then be executed by the processor (on-board or remote to the wearable device, e.g. the knee brace 204-1) to determine motion and/or state, e.g. squatting, of the wearer when he/she is using the device.

In an embodiment of the invention, the wearable device may be configured to determine a pathological state, an injury and/or physical condition of the wearer. The wearable device may be configured to determine a probability of a pathological state, an injury and/or physical condition of the wearer. Therefore, the wearable device may be configured to determine the risk that the wearer has a disease, injury or condition, e.g. osteoarthritis, soft tissue damage or torn ligament.

In an embodiment, the person or people from which the training data is collected may have a disease, injury and/or condition. Additionally, or alternatively, the person or people from which the training data is collected may be healthy and do not have a disease, injury and/or condition.

In an embodiment, the training data may comprise labelled input data collected from a person or people that are at one or more different stages of recovery from and/or treatment for a disease, injury and/or condition.

In some forms, the group of people may comprise at least one person with a disease, injury and/or condition, and at least one other person that is healthy.

In one example, the probability of the state, injury or condition can be determined using Bayesian statistics or other probabilistic modelling approaches. In another example, a support vector machine can be used to determine a pathological state, injury or condition. For example, the algorithm could comprise a support vector machine to determine if a person has a torn ligament or arthritis based on knee kinematics and load patterns during walking. The training data which may configure or train the algorithm may be collected from at least one person with a knee condition, e.g. a torn knee ligament or arthritis, and at least one person without the knee condition. For example, a variation in step length, e.g. short, long, short, may be determined by the wearable device as being indicative of the knee condition. In another example, a shaky squatting motion may be indicative of a knee ligament injury.

Prompted Configuration

In embodiments, the training data used to configure the algorithm may be generated by the at least one sensor of the wearable device, e.g. knee brace.

In embodiments, the processor is configured to operate in a configuration or training mode. In the configuration or training mode, the wearer performs a predefined motion whilst wearing the wearable device, e.g. the wearer is prompted in one or more ways to perform the predefined motion. This configuration or training mode may be a motion detection mode. Input data indicative of the predefined motion is generated by the sensor(s) and transmitted to the processor. The processor can calculate one or more parameters indicative of the predefined motion based on the input data received. The processor is configured to then label the parameter(s) with that mode. This may form the training data which may configure the algorithm as described above. Examples of this embodiment of the invention are set out in more detail below.

In another embodiment, the processor may be configured to operate in a physiological state detection mode. In this mode, input data indicative of the predefined state is generated by the sensor(s) and transmitted to the processor. The processor can calculate one or more parameters indicative of the predefined state based on the input data received. The processor is configured to then label the parameter(s) with that mode. This may form the training data which may configure the algorithm as described above.

In an embodiment, configuration of the algorithm may comprise pre-loading the processor with a generic algorithm model as described above, and new user-specific input data is collected from the wearer during the configuration or training mode of use such that the algorithm model may be configured for the wearer. The input data collection may occur automatically upon first use, e.g. when the wearer first walks with the knee brace on.

The configuration may be carried out by a processor on-board the wearable device or a processor located remote from the wearable device. As illustrated in step 606 a set of labelled input data is collected from the new wearer at a predetermined or designated time and used to configure the algorithm in step 608. Further labelled input data sets may be collected and used to configure the algorithm, wherein this configuration is performed by a processor onboard the wearable device. For example, a new wearer using the device may be prompted via the wearable device or an associated device such as a smart phone to perform a prescribed action, for example walk for one minute. The wearer may then acknowledge this instruction and performs the prescribed action. During the action the sensors collect input data which is automatically labelled as, for example, "walking" input data. "Walking" input data can then be transmitted from the sensor for configuration by the processor of the device or another processor capable of carrying out configuration.

In one example, the input data is processed by a selected algorithm model architecture (e.g. neural network) with a set of hyper parameters, and a determination is made, and based on this determination, the algorithm model's hyper parameters are iterated to improve the accuracy of the algorithm's determination. The model architecture may also have a fixed set of hyper parameters and the model parameters may be updated. This configuration process may be repeated until the algorithm model's accuracy obtains a pre-determined or designated level. The configured algorithm model parameters are then updated on the processor on-board the wearable device or transmitted to the wearable device from the other device which carried out the configuration.

The configuration process may be carried out in near real-time. Input data may be collected and the configuration may be performed on a step-by-step or activity-by-activity basis. Input data from an activity whilst performing it or after completing it may be used for the configuration process. The near real-time configuration may be carried out continuously as new labelled input data is collected continuously, e.g. after each activity, the input data from each activity is used to perform the configuration in near real-time. Alternatively, the configuration may be carried out in batches. In a batch configuration process, the configuration step is carried out at predetermined or designated times, e.g. input data collected from a day of walking is used for the configuration. The batch configuration may comprise using input data collected from a range of activities performed by the wearer, e.g. 100 steps and a day of walking and batch configuration is carried out using this input data.

The wearable device may comprise a User Interface (UI) configured to facilitate the collection, transmission and/or processing of input and output data, e.g. the smart phone 106-1 illustrated in FIG. 5, may operate an application comprising a UI which is capable of interfacing with the remote processor 114 of processing system 110 or the on-board processor 304. The UI may be a UI of the wearable device itself and/or a UI of a remote computing device such as a smart phone or smart watch which is connected to the wearable device. The UI may be used to prompt the collection of input data using the wearable device and send the input data to a remote cloud-based server for data storage, processing and display.

The algorithm may be configured using input data collected from the wearer in a set of activities which may be designated to the wearer via the UI. For example, the collected input data is labelled as "walking" input data after the UI prompts the wearer to walk for five minutes upon first use of the device.

The wearable device or remote computing device may be configured to allow manual or automatic data transmission from the wearable device to the cloud-based server, either directly or via the remote computing device, for configuration, e.g. depending on the nature of the activity or the injury being treated with the wearable device such as a knee brace, the frequency at which data is sent from the wearable device to the cloud-based server may be automatic or manually selected, e.g. once a day, week, or month, or on pre-selected dates/times by the clinician or therapist, or selected or adjusted remotely by clinician or therapist via a remote computing device associated with the wearable device.

Manually Prompted Labelling of Data

Input data generated by the sensor may be labelled manually and the labelled input data may then be used for configuration. The wearer may instruct the device that he/she is performing or about to perform a specific motion or activity such that the input data generated by the sensor is labelled according to the motion or activity. The processor is configured to then enter into the training and/or configuration mode, as described above. In one example, the wearer uses a UI of a smart phone 106-1 or smart watch 106-2 which is one of the wearable devices of the motion/state determination system 100, 300 which is used by the wearer, or connected to the wearable device wherein the wearer instructs the device that he/she is performing or about to perform a set of activities such as walking or squats. As a result, the input data generated by the sensor is labelled as "walking" or "squatting", and the labelled input data is then used for configuration. The labelled input data may be configured by the device or transmitted to the remote cloud-server for optimisation.

Automatic Labelling of Data

Input data generated by the sensor(s) may be labelled automatically and the labelled input data may then be used for configuration. The processor may be configured to automatically detect a specific motion or activity such that the input data generated by the sensor(s) is labelled according to the motion or activity. In one example, the algorithm may be configured automatically in a continuous or periodic manner without the need for the wearer to label input data via the UI as described above. The algorithm may detect an activity and labels the activity as "walking" and the labelled input data is then used to configure the algorithm. A portion of the labelled input data may be selected and used to configure the algorithm. Automatic labelling of input data is useful if the pattern of activity of the wearer is changing over time, e.g. when the wearer is recovering from a limp. The algorithm is automatically configured by using the newer training data for configuration which overwrites the older training data used previously for configuration.

Decision-Making Relating to Location of the Configuration Performance

Configuration of the algorithm may be performed using the cloud computing system, the remote computing device, and/or on the wearable device itself. As described above, in embodiments, the processor may be configured to receive training data indicative of the motion parameter and/or the physiological parameter and to configure the algorithm based on the training data it receives. In embodiments, the processor of the wearable device may be configured to receive data indicative of the algorithm from a remote processor. For example, the algorithm configuration, as described herein, may be carried out remotely from the wearable device, e.g. on the remote processor. The remote processor may be configured to receive training data indicative of the motion parameter and/or the physiological parameter and to configure the algorithm based on the training data.

In one example, the input data may be transmitted to the cloud-based server, wherein the algorithm may be configured, and the updated or configured algorithm model parameters are then sent to the wearable device for implementation in the algorithm.

In another example, the configuration is carried out by the remote processor 114, e.g. a computer program/software/application on a smart phone 106-1 or other remote computing device 124, and thereafter the configured algorithm model parameters are transmitted to the wearable device, e.g. knee brace 102-1 for implementation.

In another example, the configuration is carried out by the processor 304 configured on-board the wearable device, e.g. knee brace 102-1.

The processor may be configured to determine whether to configure the algorithm based on the training data received and/or based on the data indicative of the algorithm received from the remote processor. In other words, the processor may be configured to decide where configuration of the algorithm is to be performed, i.e. on the wearable device's on-board processor and/or the remote processor.

The wearable device may comprise a determination processor configured to make a decision relating to where configuration may be performed, whether it may be partially or wholly performed on-board the wearable device and/or the remote computing device and/or the cloud computing system.

When making the decision, the processor is configured to determine whether the configuration required is substantially simple, e.g. input data set is small, and if it is, the configuration may be carried out on-board the wearable device, whereas if the processor determines that a more complex configuration is required, e.g. the input data set is large, the configuration may be carried out in the cloud-based server or remote computing device.

The rules relating to the decision may be based on the accuracy of the current state of the algorithm model, wherein the processor is configured to test the confidence or accuracy of the algorithm in determining an output against manually labelled input data collected from the sensors. The rule may also or alternatively be based on the complexity of the activity to be determined. The processor may be configured to apply at least one threshold value of a factor, such as accuracy or complexity, wherein the threshold may facilitate the decision-making process. For example, if the accuracy or complexity calculated exceeds the threshold, a first decision is made, and if the accuracy or complexity calculated is below the threshold, a second decision is made. The thresholds may comprise a pre-determined value or range, e.g. thresholds set at 5%, 50% and 70%, wherein the accuracy which is calculated may be above or below one or more of the thresholds and a decision is made as to where configuration should be performed and/or the extent of configuration to be performed based thereon. For example, the algorithm model is used to determine if a person is walking based on the input data collected by the sensor, wherein the input data is manually labelled as "walking" by the wearer through the associated software application's UI on his/her smart phone. If the algorithm model determines that the wearer is walking, then no configuration may be required at that stage. If the determination made by the algorithm is 50% accurate, this indicates that the algorithm may require partial configuration which may be performed on-board the wearable device and/or the remote computing device. If the determination is 5% accurate then a full configuration may need to be performed using the cloud-based server.

Furthermore, based on the confidence or accuracy result, the amount of new labelled input data required for configuration may be defined and communicated to the wearer, e.g. if the accuracy is 50% then two minutes of new labelled input data is required and a request can be sent to the wearer's smart phone instructing him/her to collect the input data via the UI. If the accuracy is 5% then twenty minutes of labelled input data may be required for configuration.

The confidence or accuracy of the algorithm model's determination may be used to determine how much more labelled input data is needed for configuration and where the configuration can be performed. For example, if the algorithm model is 40% accurate, ten minutes of labelled input data may be required, and the configuration needs to be performed by a cloud-based server or remote processor.

The accuracy of the algorithm model may be verified by the wearer or an observer via the UI. The UI may allow the wearer to provide feedback to the processor of the wearable device as to how accurate it is in determining an activity. For example, a processor triggers a UI on the wearable device or another device associated with the wearer to display a message which asks the wearer, "are you walking now, or, are you doing squats?", wherein the wearer may verify the activity by answering the question by voice or text message response, or pressing a button on the UI which provides the answer, and thereafter the answer provided may be compared to the activity determined by the algorithm which in turn may facilitate decision-making relating to whether or not the algorithm model requires configuration. For example, if the determination is correct then no further labelled input data is required, and no configuration is necessary. Alternatively, if the determination is not verified by the wearer, an additional one minute of labelled input data may be required and the wearer is prompted to perform the activity to collect the further input data required. The input data used for verification may also be labelled and used in the configuration process if configuration is required, e.g. if the verification step asks the wearer via a message displayed on the UI, "are you walking?" and the wearer answers "no" by responding via the UI, then the collected input data can be labelled as "not-walking".

Periodic Configuration

The processor may be configured such that configuration of the algorithm may be performed periodically, e.g. the first time the wearer wears the wearable device, the first walk after an injury, once per week, or when the algorithm becomes less confident or accurate as the wearer experiences changes in activity, e.g. as the wearer experiences a change in gait whilst recovering from a limp.

The loss in confidence or reduction in accuracy which triggers configuration of the algorithm may be measured against a predetermined or designated threshold.

During periodic configuration, the input data collected by the sensor is labelled each time the wearer is prompted to collect input data based on one or more rules defined in the processor, e.g. the wearer may be prompted to collect input data at first use, once per week, or when the algorithm becomes less confident or accurate.

Configuration of Wearable Device Using Another Wearable Device

The system 100 described above may comprise a further wearable device, the further wearable device comprising a body portion configured to be worn by the wearer, and at least one sensor mounted to the body portion. The at least one sensor may be configured to, while the further wearable device is being worn detect a further motion parameter of the wearer and/or a further physiological parameter of the wearer, and generate training data indicative of the further motion parameter and/or the further physiological parameter. The further wearable device may further be configured to output the training data to the processor of the wearable and/or the remote processor of the system.

In an example, the wearable device of the system 100 is a wearable device configured to be worn on a wrist of the wearer, e.g. a smart watch 106-2, and the further wearable device is a joint brace, e.g. knee brace 102-1. In another example, the wearable device of the system 100 is a wearable device configured to be worn on a foot of the wearer, e.g. a smart insole 108-2 or smart shoe, and the further wearable device is a joint brace, e.g. knee brace 102-1. In other examples the wearable device and the further wearable device may be any combination of any of the following devices: orthosis or exoskeleton device (e.g. knee, elbow, shoulder, spine or back, ankle and/or wrist brace), smart watch, smart prosthetic, smart phone, smart shoe.

The remote processor, e.g. remote processor/processing system 110 may be configured to receive the training data from the further wearable device and the training data from the wearable device. The training data from the further wearable device and the training data from the wearable device may be generated while the further wearable device and the wearable device are worn simultaneously by the wearer. The remote processor may configure the algorithm based on a comparison of the training data from the further wearable device and the training data from the wearable device so that the algorithm is configured, at a future time, to be executed by the processor to determine the nature of motion and/or the physiological state of the wearer based on the input data from the wearable device and without receiving further data from the further wearable device at the future time.

In embodiments, the processor may be configured to execute the algorithm to determine the nature of motion and/or the physiological state when the further wearable device is not worn by the wearer.

By way of further explanation/example, the processor may be configured such that the training data indicative of the motion parameter and/or the physiological parameter received from the wearable device, e.g. knee brace 102-1, may be used to configure the algorithm for use on another wearable device, e.g. smart phone 106-1 or smart watch used by the same wearer, e.g. training data indicative of gait or activity of the wearer is collected from a knee brace 102-1 and is used to configure the algorithm that is executed by a processor which is on-board or in communication with (i.e. remotely connected) a smart phone 106-1 or smart watch 106-2 to determine gait or activity of the wearer, for example range-of-motion while walking. The training data may be collected and transmitted from the wearable device, e.g. knee brace 102-1 to one or more other wearable device, e.g. smart phone 106-1 or smart watch for configuration on the other wearable device, and/or the labelled input data and raw data from the wearable device may be transmitted to a remote processor 114 or cloud-based server for configuration and thereafter the configured algorithm model parameters may be transmitted back to the other wearable device 106-1, and/or the labelled input data may be configured on the wearable device, e.g. 102-1 itself and thereafter the configured algorithm model parameters may be transmitted to the other wearable device, e.g. smart phone or smart watch for execution thereon without the need for the device that collected the training data.

The determination made by the algorithm of the wearable device may be used to provide training data for another wearable device. This may be useful because the wearable device used to provide the training data to the other wearable device may not be feasible for longer-term use, e.g. a knee brace 102-1 according to an embodiment of the invention which may only be used for a period of time may be used to determine the wearer's activity, and the label provided to that input data by the knee brace 102-1 may be used to label input data collected by an accelerometer of the wearer's smart phone 106-1 or smart watch. This can then be used long term for data collection.

In an example, the knee brace input data and predefined patient data (e.g. height, weight etc.) may be used to detect gait spatiotemporal parameters and/or determine activity. This input data is labelled based on the gait spatiotemporal parameters detected and/or activity determined. The labelled input data provides the training data used to train the algorithm that can be deployed on the patient's smart watch, for example so functional range-of-motion during walking can be determined using the watch long-term without the knee brace.

The training can be done prior with different wearers offline (i.e. pretrained) or can be subject-specific i.e. each person can do some data collection to train the algorithm. Training can also be done at regular intervals, e.g. re-trained once per week or month as the person's gait patterns change, or can be trained opportunistically when the patient happens to be wearing the knee brace at the same time as the watch.

Labelling of Wearable Device Input Data Using Another Device

Labelling of input data generated by the wearable device may be performed by another computing device. The other computing device may comprise another wearable device, or any suitable remote computing device associated with the wearable device, wherein the input data collected by the wearer device may be labelled using input data collected from the other wearable device or remote computing device. For example, the wearer or an observer such as a therapist may record a video of the wearer performing an activity using a smart phone 106-1 which comprises a software application compatible with the wearable device 102-1, wherein the data collected in the video of the wearer is processed and used to label the input data collected from the wearable device 102-1 during the activity.

The labelled data may then be used for configuring the algorithm on the wearable device's on-board processor 304, e.g. the video data collected from the wearer's smart phone 106-1 can be used to label data from the knee brace 102-1 in order to configure and update the algorithm model on the knee brace 102-1. Additionally, or alternatively, video data collected from the wearer's smart phone 106-1 which is captured while the wearer is wearing the smart watch 106-2, may be used to label the input data collected from the smart watch 106-2 to train the algorithm executed by the processor (on-board or remote the smart watch) to determine the motion/activity when using the smart watch 106-2.

The other device may be a non-wearable device, e.g. personal computer 124 that is periodically connected to the wearable device in order to collect and transmit input data for labelling and/or configuration of the wearable device. For example, the non-wearable device may be a computing device such as a tablet computer, laptop or personal computer (PC) 124 located in a clinician or therapist's room which comprises software which is associated with the wearable device 102-1.

The input data generated may be labelled in real-time using other inputs. Observers may indicate on a computing device, e.g. computer 124 or the UI of a smart phone 106-1 what activity is being performed by the wearer, e.g. buttons on the UI displayed on a smart phone 106-1 may be pressed by a therapist or observer. The input data may be labelled by the wearer himself/herself, e.g. the wearer indicates on his/her smart phone UI which activity he/she is going to perform, currently performing or has completed performing.

Input data may also be labelled using inputs such as buttons, voice commands, Global Positioning System (GPS), amongst others which may be configured on the wearable device and/or the remote computing device associated with the wearable device. For example, the input data is labelled using voice commands wherein the wearer or an observer uses a voice command to instruct the wearable device what activity is about to be performed, is currently being performed, or has been completed. The activity related input data may be labelled using other suitable sensors, e.g. GPS on a smart phone, topological maps or otherwise.

In an embodiment of the invention, the sensor(s) collect input data wherein the input data may be stored on-board, and the processor may comprise a dynamic communication algorithm that only transmits data to a software application/computer program and/or a cloud-based server if a threshold is reached, e.g. more than ten steps are completed by the wearer, or more than five minutes of activity are performed by the wearer. Alternatively, the updates may be controlled by a minimum time threshold, e.g. updates are not sent to the cloud-based server more than once per minute. The dynamic communication algorithm aids battery-life and control of the transmission and storage of input data on the wearable device. The thresholds can be varied based on wearer or clinician/therapist preference, injury type or other suitable criteria.

Another example of the non-wearable device is a load sensor, e.g. a weighing scale. The patient may step onto the load sensor. For example, the patient may be wearing the wearable device (e.g. knee brace 102-1 or smart watch 106-2) and performing an activity such as walking, during which activity he/she may step onto the load sensor, one or more times. The load sensor may provide labelled data to train the algorithm to be executed by the processor to determine motion/state, e.g. walking, based on the input data received from the sensor(s) of the wearable device (e.g. knee brace 102-1 or smart watch 106-2). In an example, one or more of an accelerometer and gyroscope of the wearable device may measure ground reaction force, load/pressure distribution and joint loads in one or more axes based on the labelled data.

The processor may be configured to execute the algorithm so that the output data generated is a percentage of weight bearing the patient is doing, e.g. 50% weight bearing. This percentage is based on labelled data collected from healthy people with equivalent size, demographics and/or condition to the patient. For example, the ground reaction force, load/pressure distribution and joint loads measured by the smart watch 106-2 as described above, may be compared to the weight bearing labelled data collected as described above. The processor may be configured to determine the percentage of weight bearing by the patient based on this comparison.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The entire disclosures of all applications, patents and publications cited above and below, if any, are herein incorporated by reference.

Reference to any prior art in this specification is not, and should not be taken as, an acknowledgement or any form of suggestion that that prior art forms part of the common general knowledge in the field of endeavour in any country in the world.

Aspects of the present technology may also be said broadly to consist in the parts, elements and features referred to or indicated in the specification of the application, individually or collectively, in any or all combinations of two or more of said parts, elements or features. Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present technology.

The invention claimed is:

1. A knee brace for determining a nature of motion and/or a physiological state of a wearer, the knee brace comprising:
- a first brace portion configured to be mounted superior to a knee joint of the wearer;
- a second brace portion configured to be mounted inferior to a knee joint of the wearer; and
- at least one sensor mounted to the first brace portion and/or the second brace portion, wherein the at least one sensor comprises an inertial measurement unit (IMU) comprising at least one accelerometer, wherein the at least one sensor is configured to, while the knee brace is being worn:
  - detect a motion parameter of the wearer; and
  - generate input data indicative of the motion parameter, wherein the input data comprises accelerometer data,
- the knee brace further comprising a processor configured to:
  - receive the input data from the at least one sensor;
  - data execute an algorithm to determine that the wearer is walking, wherein the algorithm comprising comprises detecting a first event in the accelerometer data indicative of a heel strike event, detecting a second event in the accelerometer data, and detecting a repeat of the first event in the accelerometer data, and making a determination that the wearer is walking based on the detected sequence of events in the accelerometer data; and
  - determine gait spatiotemporal parameters of the wearer based at least in part on the determination that the wearer is walking.

2. A system for determining that a wearer of a knee brace is walking, the system comprising:
- a knee brace comprising:
  - a first brace portion configured to be mounted superior to a knee joint of the wearer;
  - a second brace portion configured to be mounted inferior to a knee joint of the wearer; and
  - at least one sensor mounted to the first brace portion and/or second brace portion, wherein the at least one sensor comprises an inertial measurement unit (IMU) comprising at least one accelerometer, wherein the at least one sensor is configured to, while the knee brace is being worn:
  - detect a motion parameter of the wearer; and
  - generate input data indicative of the motion parameter, wherein the input data comprises accelerometer data,
- the system further comprising a processor configured to:
  - receive the input data from the at least one sensor;
  - execute an algorithm to determine that the wearer is walking, wherein the algorithm comprises detecting a first event in the accelerometer data indicative of a heel strike event, detecting a second event in the accelerometer data and detecting a repeat of the first event in the accelerometer data, and making a determination that the wearer is walking based on the detected sequence of events in the accelerometer data; and
  - determine gait spatiotemporal parameters of the wearer based at least in part on the determination that the wearer is walking.

3. The knee brace of claim 1, wherein the second event is a toe-off event detected by the processor based on the accelerometer data, and wherein the repeat of the first event is detected by the processor based on the accelerometer data.

4. The knee brace of claim 1, wherein the knee brace is configured to measure functional range-of-motion of the wearer.

5. The knee brace of claim 4, wherein the at least one sensor is configured to measure a maximum knee angle and a minimum knee angle.

6. The knee brace of claim 5, wherein the at least one sensor comprises a first sensor module located in use below the knee joint of the wearer and a second sensor module located in use above the knee joint of the wearer.

7. The knee brace of claim 6, wherein the first sensor module and the second sensor modules are IMUs.

8. The knee brace of claim 5, wherein the at least one sensor comprises a first sensor module located in use above or below the knee joint of the wearer and a second sensor module located in use on the knee joint of the wearer.

9. The knee brace of claim 8, wherein the first sensor module and the second sensor modules are rotary sensors.

10. The knee brace of claim 1, wherein the processor is configured to determine the gait of the wearer.

11. The knee brace of claim 10, wherein the processor is configured to:
- detect a first event;
- detect a second event;
- detect a repeat of the first event;
- calculate distance travelled;
- calculate walking velocity;
- determine functional range-of-motion; and
- collect and/or aggregate data over multiple cycles.

12. The knee brace of claim 1, wherein the processor is configured with an AI to determine that the wearer is walking.

13. The system of claim 2, wherein the processor is located remote from the knee brace.

14. The system of claim 2, wherein the second event is a toe-off event detected by the processor based on the accelerometer data, and wherein the repeat of the first event is detected by the processor based on the accelerometer data.

15. The system of claim 2, wherein the knee brace is configured to measure functional range-of-motion of the wearer.

16. The system of claim 15, wherein the at least one sensor is configured to measure a maximum knee angle and a minimum knee angle.

* * * * *